US008435280B2

(12) United States Patent
Gregorich

(10) Patent No.: US 8,435,280 B2
(45) Date of Patent: May 7, 2013

(54) FLEXIBLE STENT WITH VARIABLE WIDTH ELEMENTS

(75) Inventor: Daniel J. Gregorich, Mound, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 195 days.

(21) Appl. No.: 11/095,004

(22) Filed: Mar. 31, 2005

(65) Prior Publication Data
US 2006/0224231 A1    Oct. 5, 2006

(51) Int. Cl.
*A61F 2/82*    (2006.01)

(52) U.S. Cl.
USPC ......................................... 623/1.15

(58) Field of Classification Search ............... 623/1.1, 623/1.11, 1.15, 1.34
See application file for complete search history.

(56) References Cited

U.S. PATENT DOCUMENTS

| 5,195,969 | A |   | 3/1993  | Wang et al.      |         |
|-----------|---|---|---------|------------------|---------|
| 5,270,086 | A |   | 12/1993 | Hamlin et al.    |         |
| 5,366,504 | A |   | 11/1994 | Andersen et al.  |         |
| 5,636,641 | A | * | 6/1997  | Fariabi ........... | 623/1.1 |
| 5,674,242 | A |   | 10/1997 | Phan et al.      |         |
| 5,733,303 | A |   | 3/1998  | Israel et al.    |         |
| 5,780,807 | A |   | 7/1998  | Saunders         |         |
| 5,807,404 | A |   | 9/1998  | Richter          |         |
| 5,876,449 | A |   | 3/1999  | Starck et al.    |         |
| 5,922,020 | A |   | 7/1999  | Klein et al.     |         |
| 5,925,061 | A | * | 7/1999  | Ogi et al. ....... | 623/1.2 |
| 6,001,123 | A |   | 12/1999 | Lau              |         |
| 6,042,606 | A |   | 3/2000  | Frantzen         |         |
| 6,190,406 | B1|   | 2/2001  | Duerig et al.    |         |
| 6,203,569 | B1| * | 3/2001  | Wijay ............ | 623/1.15|
| 6,264,687 | B1|   | 7/2001  | Tomonto          |         |
| 6,409,754 | B1|   | 6/2002  | Smith et al.     |         |
| 6,451,052 | B1|   | 9/2002  | Burmeister et al.|         |
| 6,485,507 | B1|   | 11/2002 | Walak et al.     |         |
| 6,540,774 | B1| * | 4/2003  | Cox .............. | 623/1.15|
| 6,540,777 | B2| * | 4/2003  | Stenzel .......... | 623/1.15|
| 6,565,599 | B1|   | 5/2003  | Hong et al.      |         |
| 6,676,987 | B2|   | 1/2004  | Zhong et al.     |         |
| 6,726,712 | B1|   | 4/2004  | Raeder-Devens et al. |     |
| 6,818,014 | B2|   | 11/2004 | Brown et al.     |         |
| 6,896,696 | B2| * | 5/2005  | Doran et al. ..... | 623/1.15|
| 7,147,660 | B2| * | 12/2006 | Chobotov et al. .. | 623/1.14|
| 7,204,848 | B1|   | 4/2007  | Brown et al.     |         |

(Continued)

FOREIGN PATENT DOCUMENTS

| EP | 0 734 698 | 3/1996 |
| EP | 0734698   | 3/1996 |

(Continued)

OTHER PUBLICATIONS

Schetsky, L. McDonald, "Shape Memory Alloys", Encyclopedia of Chemical Technology (3rd ed.), John Wiley & Sons, 1982, vol. 20. pp. 726-736.

*Primary Examiner* — Brian E. Pellegrino
(74) *Attorney, Agent, or Firm* — Vidas, Arrett & Steinkraus, P.A.

(57) ABSTRACT

Medical devices, such as endoprostheses, are disclosed. In some embodiments, an endoprosthesis includes a circumferentially-oriented band including two curved portions and a first portion connecting the two curved portions, the first portion having a first width and at least one curved portion having a second width; and a connector extending from the band; wherein the second width is greater than the first width.

28 Claims, 6 Drawing Sheets

U.S. PATENT DOCUMENTS

| | | |
|---|---|---|
| 7,229,471 B2 * | 6/2007 | Gale et al. .................... 623/1.15 |
| 7,344,560 B2 * | 3/2008 | Gregorich et al. ........... 623/1.15 |
| 2002/0082681 A1 | 6/2002 | Boylan et al. |
| 2002/0144757 A1 | 10/2002 | Craig et al. |
| 2003/0004567 A1 | 1/2003 | Boyle et al. |
| 2003/0018380 A1 | 1/2003 | Craig et al. |
| 2003/0055485 A1 | 3/2003 | Lee et al. |
| 2003/0077200 A1 | 4/2003 | Craig et al. |
| 2003/0185895 A1 | 10/2003 | Lanphere et al. |
| 2004/0143317 A1 | 7/2004 | Stinson et al. |
| 2004/0243218 A1 * | 12/2004 | Schaeffer .................... 623/1.15 |
| 2005/0049680 A1 | 3/2005 | Fischell et al. |

FOREIGN PATENT DOCUMENTS

| | | |
|---|---|---|
| EP | 0 934 036 | 10/1997 |
| JP | 2004-522463 | 7/2004 |
| WO | 95/26695 | 10/1995 |
| WO | WO 96/29028 | 3/1996 |
| WO | WO 97/04721 | 2/1997 |
| WO | 9818407 | 5/1998 |
| WO | WO 99/16387 | 4/1999 |
| WO | WO 02/24111 | 3/2002 |
| WO | WO 2004/058104 | 7/2004 |

* cited by examiner

FLEXIBLE STENT WITH VARIABLE WIDTH ELEMENTS

TECHNICAL FIELD

The invention relates to medical devices, such as endoprostheses (e.g., stents).

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Examples of endoprostheses include stents, covered stents, and stent-grafts.

Endoprostheses can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

The expansion mechanism may include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn.

In another delivery technique, the endoprosthesis is formed of an elastic material that can be reversibly compacted and expanded, e.g., elastically or through a material phase transition. During introduction into the body, the endoprosthesis is restrained in a compacted condition. Upon reaching the desired implantation site, the restraint is removed, for example, by retracting a restraining device such as an outer sheath, enabling the endoprosthesis to self-expand by its own internal elastic restoring force.

SUMMARY

The invention relates to medical devices, such as endoprostheses.

In one aspect of the invention, an endoprosthesis comprises: a circumferentially-oriented band including two curved portions and a first portion connecting the two curved portions, the first portion having a first width and at least one curved portion having a second width, wherein the second width is greater than the first width.

Embodiments may include one or more of the following features.

The endoprothesis can have a second width to first width ratio is greater than 1 and less than 3 (e.g. greater than 1.05 greater than 1.1, greater than 1.5, or greater than 1.75).

The endoprothesis can have curved portions and first portion including a material with a yield strength of greater than 50 kilopounds per square inch and less than 150 kilopounds per square inch. (e.g. greater than 55 kilopounds per square inch, greater than 65 kilopounds per square inch, or greater than 70 kilopounds per square inch).

The curved portions and first portions can comprise a material selected from the group consisting of stainless steel, stainless steel alloyed with a radiopaque element, nickel alloy, niobium alloy, and titanium alloy.

The circumferentially-oriented band can include a plurality of curved portions and a plurality of first portions connecting adjacent curved portions to form a generally sinusoidal pattern. The endoprosthesis can include a plurality of the circumferentially-oriented bands and a plurality of connectors, the connectors extending between adjacent bands.

The circumferentially-oriented band can include a plurality of curved portions and a plurality of first portions connecting the curved portions, each first portion further having a length; wherein each band has an aggregate curved portion width to first portion length ratio, calculated by dividing an average curved portion width by a sum of lengths of the first portions, that is greater than 0.01 (e.g. greater than 0.015).

In another aspect of the invention, an endoprothesis comprises a circumferentially-oriented band including a plurality of curved portions and a plurality of first portions connecting adjacent curved portions to form a generally sinusoidal pattern, the first portions having a first average width and the curved portions having a second average width, wherein a width ratio calculated by dividing the second average width by the first average width is greater than 1.05, and the curved portions and first portion comprise a material with a yield strength of greater than 55 kilopounds per square inch.

Embodiments may include one or more of the following features.

The width ratio can be greater than 1.1.

The curved portions and first portion can comprise a material with a yield strength of greater than 70 kilopounds per square inch.

The endoprosthesis can include a plurality of the circumferentially-oriented bands and a plurality of connectors, the connectors extending between adjacent bands.

In another aspect of the invention, an endoprothesis comprises: two first portions generally transverse to a longitudinal axis of the endoprothesis, the first portions having a first average width; and a second portion connecting the first portions, the second portion having a second average width, wherein the first average width is greater than the second average width. The second portion can be substantially parallel to the longitudinal axis. The first portions and the second portion can form angles of between about 80 and 110 degrees at their intersections.

Embodiments may include one or more of the following advantages. Without wishing to be bound by theory, it is believed that certain stents, such as those including (e.g., made from) a high yield strength material, can experience relatively high recoil when the stents are expanded against a vessel wall or crimped onto a delivery catheter. As a result, the securement of the stents to the vessel wall or the delivery catheter may be less than desired. By forming the stents with curved portions with curved portions with widths that are greater than widths of adjoining straight portions, it is believed that the strain that occurs during crimping or expansion of the stents is transferred and concentrated to the relatively small volume of material of the straight portions, which can increase the strain more along the stress-strain curve and result in plastic, rather than elastic, deformation of the stent. As a result, recoil is limited and stent securement is enhanced. Furthermore, by increasing the width of only curved portion, it is believed that flexibility is enhanced, for example, relative to stents where the widths of both the curved and straight portions are increased.

Other aspects, features, and advantages will be apparent from the description of the preferred embodiments thereof and from the claims.

DETAILED DESCRIPTION

Figure 1:
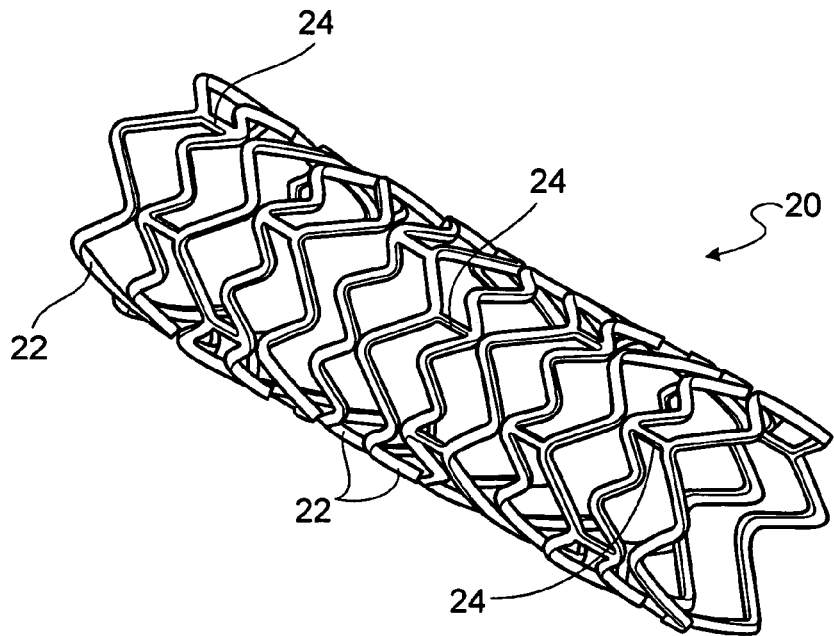
FIG. 1 is a perspective view of an embodiment of an expanded stent.

Referring to FIG. 1, a stent 20 has the form of a tubular member defined by a plurality of bands 22 and a plurality of connectors 24 that extend between and connect adjacent bands. During use, bands 22 are expanded from an initial, small diameter to a larger diameter to contact stent 20 against a wall of a bodily vessel, thereby maintaining the patency of the vessel. Examples of stents are described in Burmeister et al., U.S. Pat. No. 6,451,052.

As used herein, a band 22 refers to a portion of a stent that extends circumferentially about the stent. The band can extend completely about the circumference of a stent, for example, such that the ends of the band are joined, or the band can extend partially about the circumference. The band can extend substantially linearly or nonlinearly, for example, in an undulating pattern, a zigzag pattern (as shown in FIG. 1), or a square-wave pattern. In some embodiments, bands 22 are connected together by integrally formed connectors 24 that extend between and transversely to the bands.

As used herein, a connector 24 refers to a portion of a stent that extends from a band of the stent, for example, from a first band to an adjacent second band along the length of the stent. The connector can extend linearly (e.g., parallel to the longitudinal axis of the stent) or nonlinearly, for example, in an undulating patter or zigzag pattern.

Figure 2A:
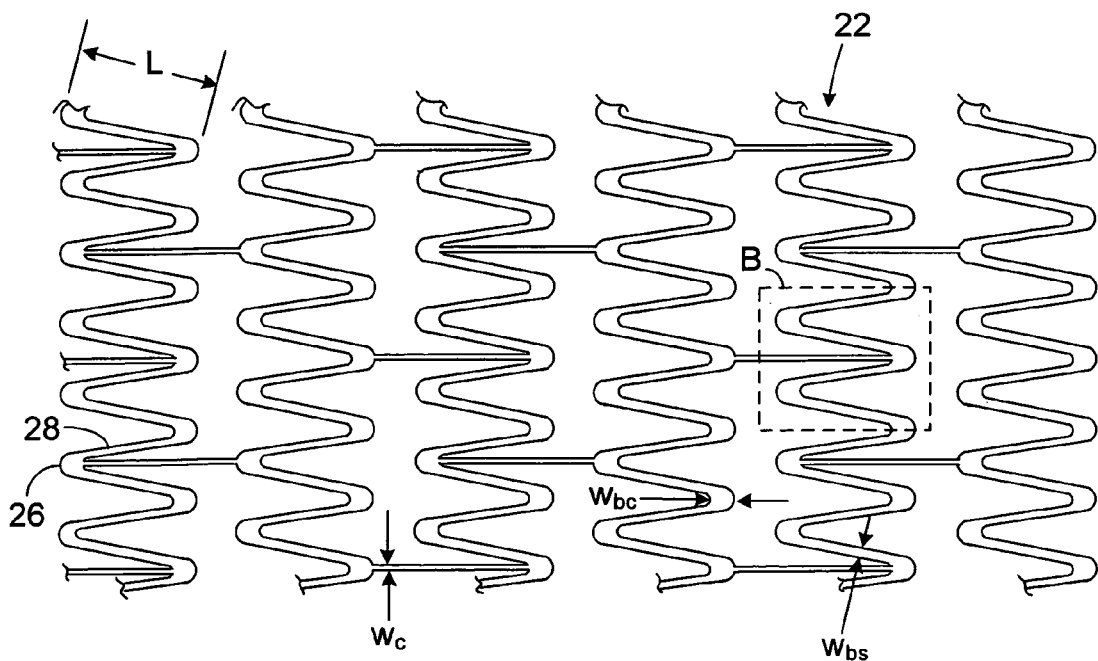
FIG. 2A is a detailed view of a section of the stent of FIG. 1.
Figure 2B:
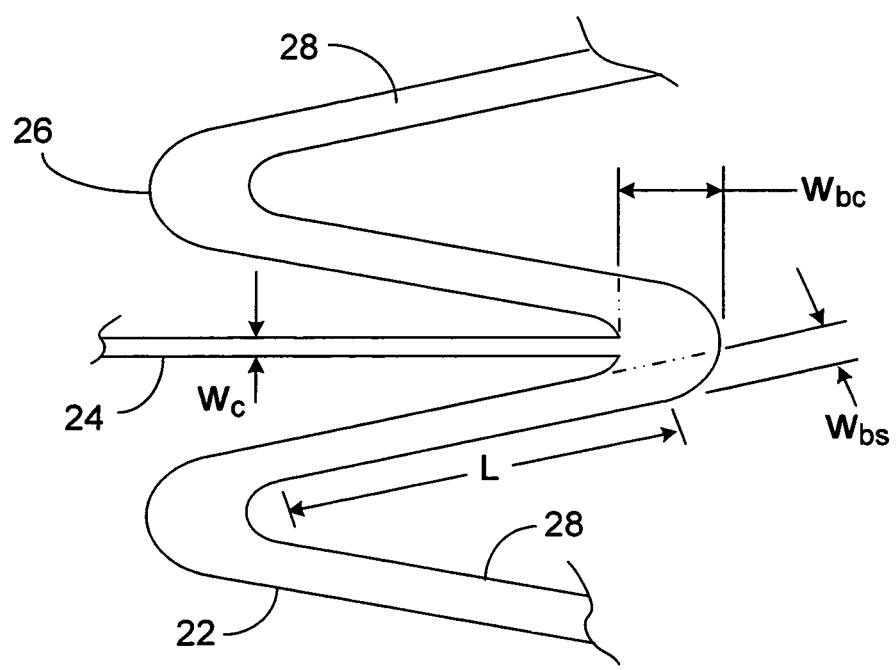
FIG. 2B is a detailed view of section B of FIG. 2A.

Referring to FIGS. 2A and 2B, bands 22 and connectors. 24 have different shapes and dimensions. As shown, bands 22 have curved portions 26 connected by straight portions 28. Curved portions 26 have a width ($W_{bc}$) that is greater than a width ($W_{bs}$) of straight portions 28. Both of these widths ($W_{bc}$, $W_{bs}$) are greater than a width ($W_c$) of connectors 24.

Without wishing to be bound by theory, it is believed that certain stents, such as those including (e.g., made from) a high yield strength material, can experience relatively high recoil when the stents are expanded against a vessel wall or crimped onto a delivery catheter. As a result, the securement of the stents to the vessel wall or the delivery catheter may be less than desired. By forming the stents with curved portions with curved portions 26 with widths ($W_{bc}$) that are greater than widths ($W_{bs}$) of adjoining straight portions 28, it is believed that the strain that occurs during crimping or expansion of the stents is transferred and concentrated to the relatively small volume of material of the straight portions, which can increase the strain more along the stress-strain curve and result in plastic, rather than elastic, deformation of the stent. As a result, recoil is limited and stent securement is enhanced. Furthermore, by increasing the width of only curved portion 26, it is believed that flexibility is enhanced, for example, relative to stents where the widths of both the curved and straight portions 26, 28 are increased.

As shown, stent 20 has a width ratio of curved portion width ($W_{bc}$) to straight portion width ($W_{bs}$) (i.e. $W_{bc}/W_{bs}$) is greater than one. The width ratio $W_{bc}/W_{bs}$ can be greater than or equal to about 1, about 1.25, about 1.5, about 1.75, about 2, about 2.25, about 2.5, about 2.75 and/or less than or equal to about 3, about 2.75, about 2.5, about 2.25, about 2, about 1.75, about, about 1.5, about 1.25. As shown, the width ($W_{bc}$) of the curved portions 26 and the width ($W_{bs}$) of straight portions 28 have substantially constant dimensions and thus the width ratio ($W_{bc}/W_{bs}$) is consistent across the stent. In some stents, these widths can vary but it is anticipated, without wishing to be bound by theory, that each individual section comprising two curved portions connected by a straight section having an individual width ratio greater than 1 and less than about 3 can cause an incremental increase in securement performance.

Bands 22 can have widths ($W_{bc}$, $W_{bs}$) ranging from about 0.03 mm to about 0.20 mm. Particular widths of band 22 can be a function of, for example, the material(s) in stent 20, the type of stent (e.g., balloon-expandable or self-expandable), and/or the desired performance. For example, a stent including 316L stainless steel can have band widths ($W_{bc}$, $W_{bs}$) of from about 0.06 mm to about 0.25 mm; a stent including an alloy of 10-60 weight percent platinum and 316L stainless steel constituents (PERSS®) can have band widths ($W_{bc}$, $W_{bs}$) of from about 0.04 mm to about 0.25 mm; and a stent including a Fe—Co—Cr—Ni alloy (such as Elgiloy, MP35N or L605) can have band widths ($W_{bc}$, $W_{bs}$) of from about 0.03 mm to about 0.20 mm; and a stent including niobium alloyed with about 1-10 weight percent zirconium, about 1-70 weight percent tantalum, or about 1-10 weight percent tungsten can have band widths ($W_{bc}$, $W_{bs}$) of from about 0.08 mm to about 0.30 mm. As shown, bands 22 include sinusoidal waves, but other embodiments, such as square waves, zigzag waves, or a plurality of connected polygons, can be used.

Connector 24 can have a width ($W_c$) ranging from about 0.03 mm to about 0.20 mm. Particular widths of connector 24 can be a function of, for example, the material(s) in stent 20, the type of stent (e.g., balloon-expandable or self-expandable), and/or the desired performance. For example, a stent including 316L stainless steel can have a connector width ($W_c$) of from about 0.05 mm to about 0.18 mm; a stent including a PERSS® alloy can have a connector width ($W_c$) of from about 0.03 mm to about 0.10 mm; a stent including an alloy having chromium and cobalt can have a connector width ($W_c$) of from about 0.02 mm to about 0.08 mm; a stent including a refractory metal can have a connector width ($W_c$) of from about 0.08 mm to about 0.20 mm; and a stent including an alloy having titanium can have a connector width ($W_c$) of from about 0.03 mm to about 0.15 mm. As shown, connectors 24 are straight, but other embodiments, such as connectors 24 that are bent, can be used. Additionally, a stent can be constructed without connectors, sharing material between adjacent bands.

In stents 20 including a plurality of curved portions 26 connected by a plurality of straight portions 28, straight portions 28 have a length (L) (see FIG. 2A). Some stents are configured with an aggregate curved portion width to straight portion length ratio, calculated by dividing an average curved portion width by a sum of lengths of the straight portions, that is greater than 0.01 (e.g., greater than 0.015.). For example, this ratio would be about $W_{bc}/12L$ (i.e. the average curved portion width $W_{bc}$ divided by the sum of the lengths of the straight portions or the number straight portions, 12, times the average length L) for the stent illustrated in FIG. 2A.

Figure 3:
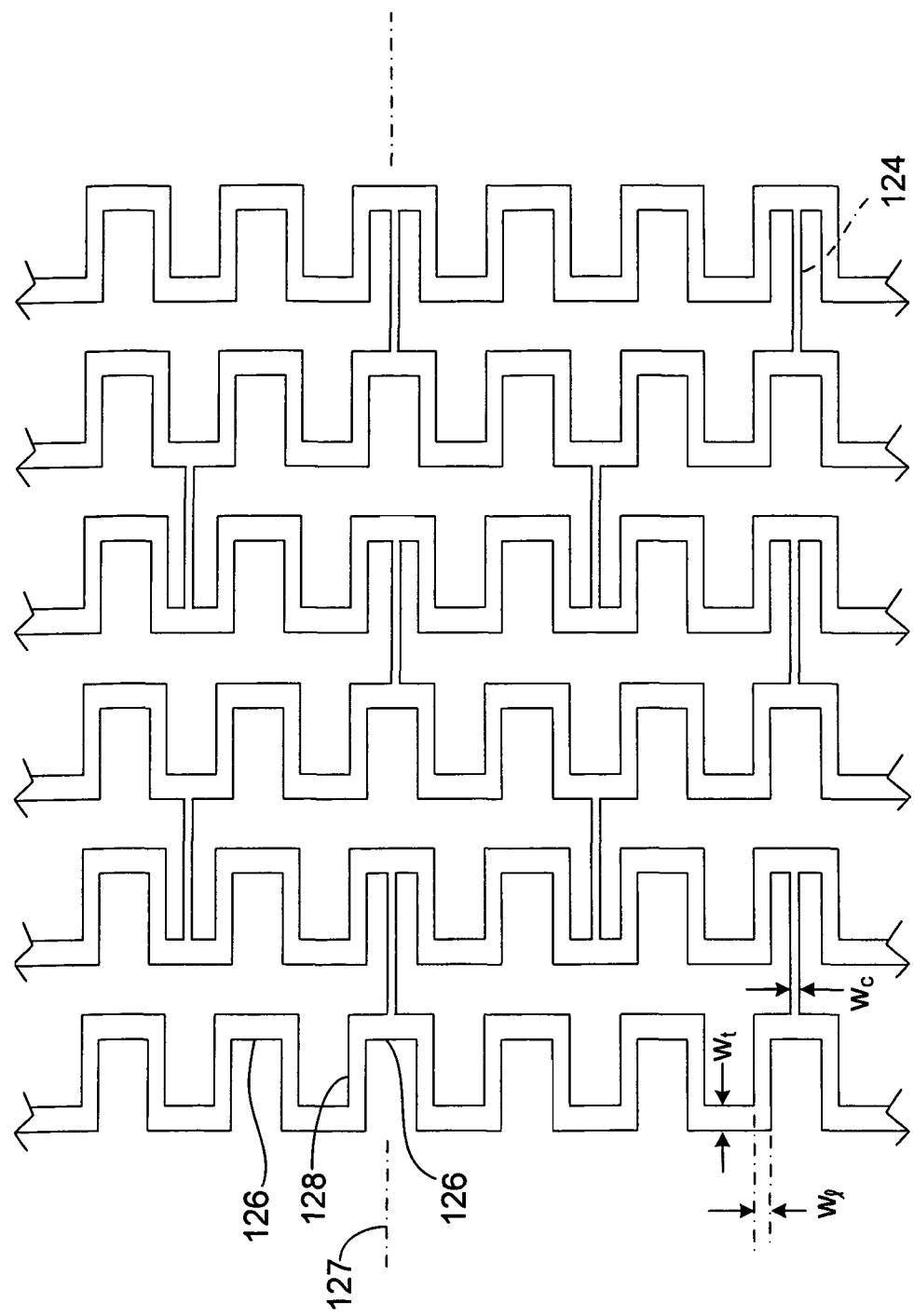
FIG. 3 is a detailed view of an alternate embodiment of a stent.

As described above, other configurations of bands and connectors are possible. For example, referring to FIG. 3, a high yield strength stent 120 can include bands 122 configured as square waves joined by connectors 124 extending between adjacent bands 122. Bands 122 include first portions 126 generally transverse to a longitudinal axis 127 of the stent and second portions 128 connecting the first portions 126. Second portions 128 are transverse to first portions 126 and parallel to longitudinal axis 127. First portions 126 and the second portions 128 can form angles of between about 80 and 110 degrees at their intersections. The first portions 126 have widths ($W_t$), the second portions have widths ($W_1$), and the connectors 124 have widths ($W_c$). As shown, the widths ($W_t$) of the first portions 126 are greater than the widths ($W_1$) of the second portions and both are greater than widths ($W_c$) of the connectors 124. Some stents, such as high yield strength stents, with varying widths ($W_t$, $W_1$) of the first 126 and second 128 portions have an average width of the first portions 126 that is greater than an average width of the second portions 128. The ratios of $W_t$ to $W_c$ ($W_t/W_c$) can range from about 1 to about 3 as described above for $W_{bc}/W_{bs}$.

Figure 4:
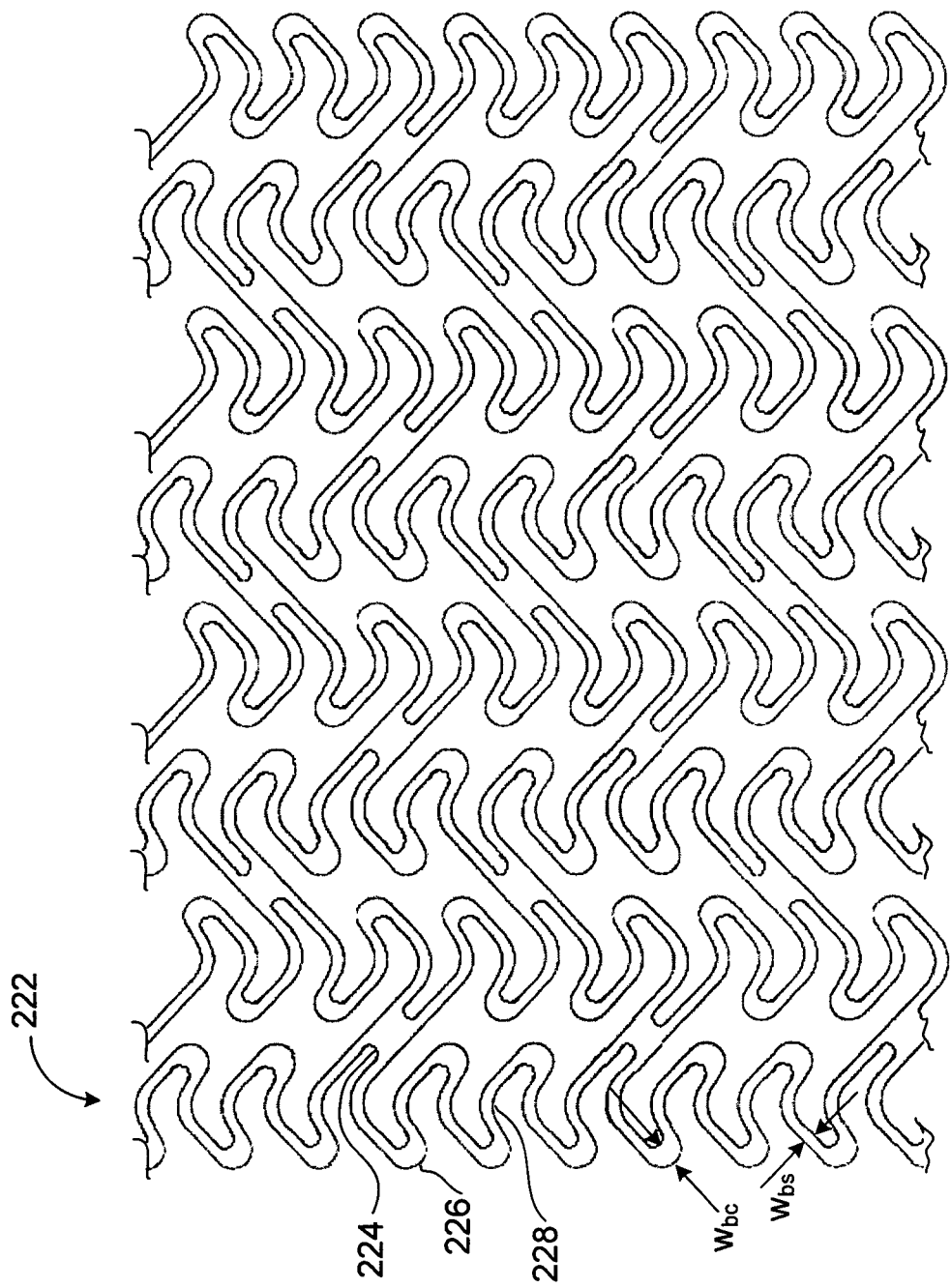
FIG. 4 is a detailed view of an alternate embodiment of a stent.
Figure 5:
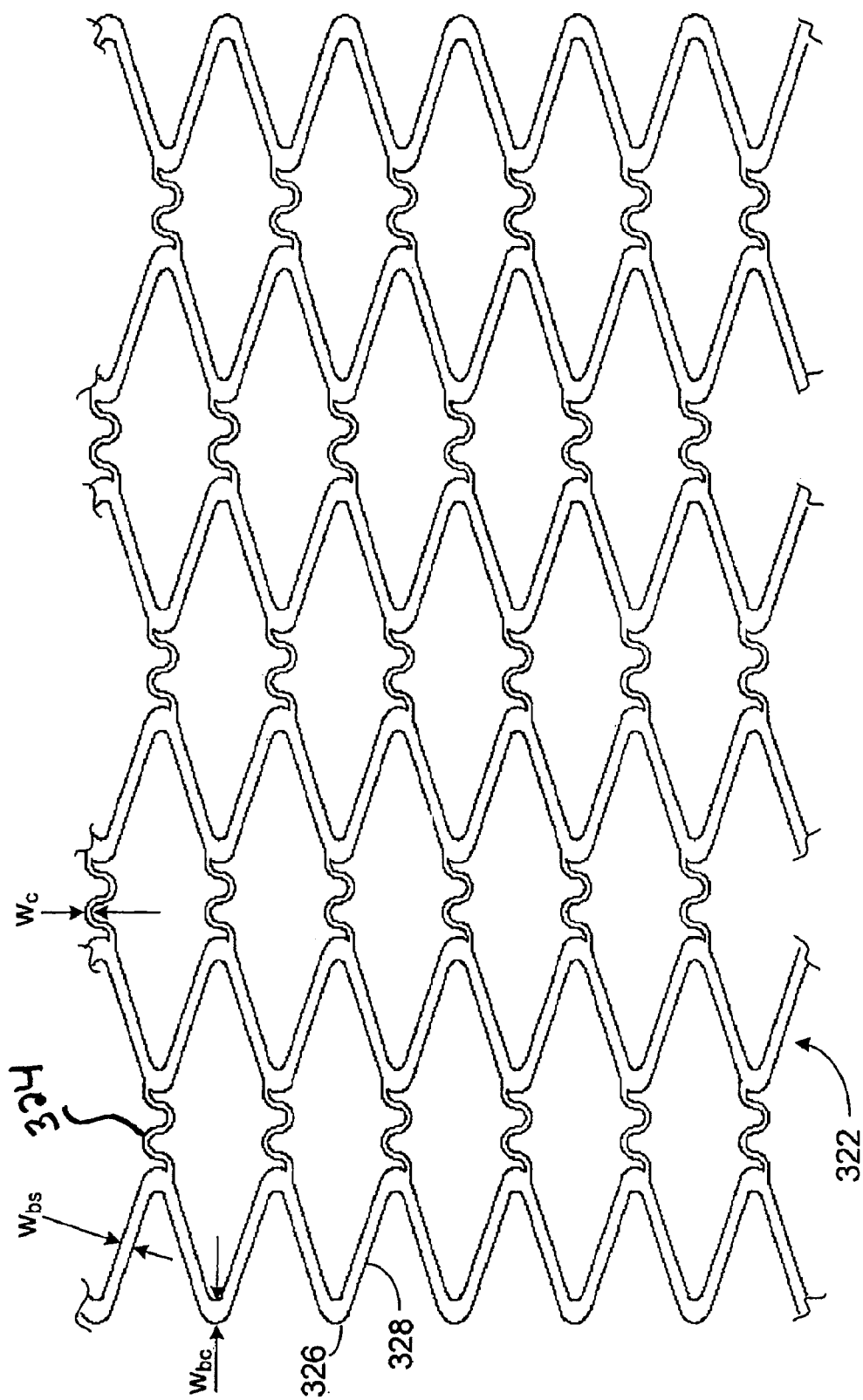
FIG. 5 is a detailed view of an alternate embodiment of a stent.
Figure 6:
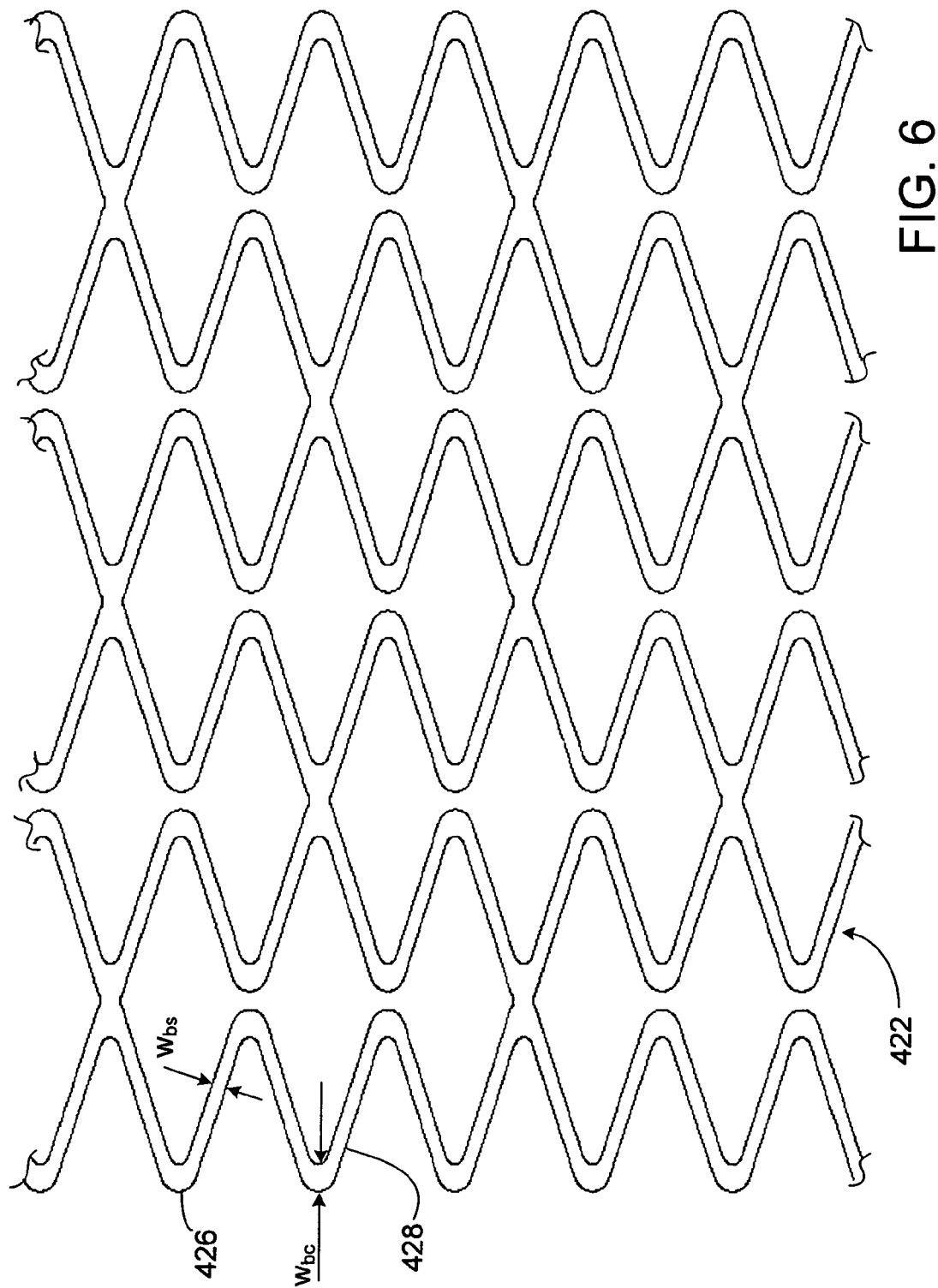
FIG. 6 is a detailed view of an alternate embodiment of a stent.

Referring to FIGS. 4-6, other configurations are possible such as bands 222, 322, 422 having curved portions 226, 326, 426 having a width $W_{bc}$ connecting adjacent straight portions 228, 328, 428 with a width $W_{bs}$ that is less than $W_{bc}$. The bands can be joined by connectors (such as bands 222, 322 joined by connectors 224, 324) or the bands can be joined without connectors (such as bands 422) Bands 22 and connectors 24 can include (e.g., be manufactured from) one or more biocompatible materials with mechanical properties so that stent 20 can be compacted, and subsequently expanded to support a vessel. In some embodiments, stent 20 can have an ultimate tensile strength (UTS) of about 20-150 ksi, greater than about 15% elongation to failure, and a modulus of elasticity of about 10-60 msi. When stent 20 is expanded, the material can be stretched to strains on the order of about 0.4. In some embodiments, bands 122 and connectors 124 include material having yield strength of from about 55 kilopounds per square inch (ksi) to about 150 ksi. The yield strength can be greater than or equal to about 60 ksi, about 70 ksi, about 80 ksi, about 90 ksi, about 100 ksi, about 110 ksi, about 120 ksi, about 130 ksi, or about 140 ksi; and/or less than about 150 ksi, about 140 ksi, about 130 ksi, about 120 ksi, about 110 ksi, about 100 ksi, about 90 ksi, about 80 ksi, about 70 ksi, or about 60 ksi. Examples of high yield strength materials include alloys (e.g., PERSS®) including stainless steel and 5-60 weight percent of one or more radiopaque elements (e.g. Pt, Ir, Au, Ta, Pd), as described in U.S. Patent Publications US-2003-0018380-A1; US-2002-0144757-A1; and US-2003-0077200-A1. Other examples of materials that provide good mechanical properties and/or biocompatibility include, for example, stainless steel (e.g., 316L and 304L stainless steel, and PERSS®), Nitinol (a nickel-titanium alloy), Elgiloy, L605 alloys, MP35N, Ti-6Al-4V, Ti-50Ta, Ti-10Ir, Nb-1Zr, and Co-28Cr-6Mo. Other materials include elastic biocompatible metal such as a superelastic or pseudoelastic metal alloy, as described, for example, in Schetsky, L. McDonald, "Shape Memory Alloys", Encyclopedia of Chemical Technology (3rd ed.), John Wiley & Sons, 1982, vol. 20. pp. 726-736; and commonly assigned U.S. patent application Ser. No. 10/346,487, filed Jan. 17, 2003.

The material(s) can include one or more radiopaque materials to provide radiopacity. Examples of radiopaque materials include metallic elements having atomic numbers greater than 26, e.g., greater than 43. In some embodiments, the radiopaque materials have a density greater than about 9.9 g/cc. In certain embodiments, the radiopaque material is relatively absorptive of X-rays, e.g., having a linear attenuation coefficient of at least 25 $cm^{-1}$, e.g., at least 50 $cm^{-1}$, at 100 keV. Some radiopaque materials include tantalum, platinum, iridium, palladium, hafnium, tungsten, gold, ruthenium, osmium, and rhenium. The radiopaque material can include an alloy, such as a binary, a ternary or more complex alloy, containing one or more elements listed above with one or more other elements such as iron, nickel, cobalt, or titanium. Examples of alloys including one or more radiopaque materials are described in U.S. Patent Application Publication US-2003-0018380-A1; US-2002-0144757-A1; and US-2003-0077200-A1.

In some embodiments, stent 20 includes one or more materials that enhance visibility by magnetic resonance imaging (MRI). Examples of MRI materials include non-ferrous metal-alloys containing paramagnetic elements (e.g., dysprosium or gadolinium) such as terbium-dysprosium, dysprosium, and gadolinium; non-ferrous metallic bands coated with an oxide or a carbide layer of dysprosium or gadolinium (e.g., $Dy_2O_3$ or $Gd_2O_3$); non-ferrous metals (e.g., copper, silver, platinum, or gold) coated with a layer of superparamagnetic material, such as nanocrystalline $Fe_3O_4$, $CoFe_2O_4$, $MnFe_2O_4$, or $MgFe_2O_4$; and nanocrystalline particles of the transition metal oxides (e.g., oxides of Fe, Co, Ni). Alternatively or in addition, stent 20 can include one or more materials having low magnetic susceptibility to reduce magnetic susceptibility artifacts, which during imaging can interfere with imaging of tissue, e.g., adjacent to and/or surrounding the stent. Low magnetic susceptibility materials include tantalum, platinum, titanium, niobium, copper, and alloys containing these elements. The MRI visible materials can be incorporated into the structural material, can serve as the structural material, and/or be includes as a layer of stent 20.

One method of making stent 20 includes forming a tube that makes up the tubular member of stent 20. The tube is subsequently cut to form bands 22 and connectors 24 to produce an unfinished stent. Areas of the unfinished stent affected by the cutting are subsequently removed. The unfinished stent is finished to form stent 20.

The tube that makes up the tubular member of stent 20 can be formed using metallurgical techniques, such as thermomechanical processes. For example, a hollow metallic member (e.g., a rod or a bar) can be drawn through a series of dies with progressively smaller circular openings to plastically deform the member to a targeted size and shape. In some embodiments, the plastic deformation strain hardens the member (and increases its yield strength) and elongates the grains along the longitudinal axis of the member. The deformed member can be heat treated (e.g., annealed above the recrystallization temperature and/or hot isostatically pressed) to transform the elongated grain structure into an initial grain structure, e.g., one including equiaxed grains. Small or fine grains can be formed by heating the member close to the recrystallization temperature for a short time. Large or coarse grains can be formed by heating the member at higher temperatures and/or for longer times to promote grain growth.

Next, bands 22 and connectors 24 of stent 20 are formed by cutting the tube. Selected portions of the tube can be removed to form bands 22 and connectors 24 by laser cutting, as described in U.S. Pat. No. 5,780,807, hereby incorporated by reference in its entirety. In certain embodiments, during laser cutting, a liquid carrier, such as a solvent or an oil, is flowed through the lumen of the tube. The carrier can prevent dross formed on one portion of the tube from re-depositing on another portion, and/or reduce formation of recast material on the tube. Other methods of removing portions of the tube can be used, such as mechanical machining (e.g., micro-machining), electrical discharge machining (EDM), and photoetching (e.g., acid photoetching).

In some embodiments, after bands 22 and connectors 24 are formed, areas of the tube affected by the cutting operation above can be removed. For example, laser machining of bands 22 and connectors 24 can leave a surface layer of melted and resolidified material and/or oxidized metal that can adversely affect the mechanical properties and performance of stent 20. The affected areas can be removed mechanically (such as by grit blasting or honing) and/or chemically (such as by etching or electropolishing). In some embodiments, the tubular member can be near net shape configuration after this is performed. "Near-net size" means that the tube has a relatively thin envelope of material that is removed to provide a finished stent. In some embodiments, the tube is formed less than about 25% oversized, e.g., less than about 15%, 10%, or 5% oversized.

The unfinished stent is then finished to form stent 20. The unfinished stent can be finished, for example, by electropolishing to a smooth finish. Since the unfinished stent can be formed to near-net size, relatively little of the unfinished stent need to be removed to finish the stent. As a result, further processing (which can damage the stent) and costly materials can be reduced. In some embodiments, about 0.0001 inch of the stent material can be removed by chemical milling and/or electropolishing to yield a stent.

Stent 20 can be of a desired shape and size (e.g., coronary stents, aortic stents, peripheral vascular stents, gastrointestinal stents, urology stents, and neurology stents). Depending on the application, stent 20 can have a diameter of between, for example, 1 mm to 46 mm. In certain embodiments, a coronary stent can have an expanded diameter of from about 2 mm to about 6 mm. In some embodiments, a peripheral stent can have an expanded diameter of from about 5 mm to about 24 mm. In certain embodiments, a gastrointestinal and/or urology stent can have an expanded diameter of from about 6 mm to about 30 mm. In some embodiments, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm. Stent 20 can be balloon-expandable, self-expandable, or a combination of both (e.g., U.S. Pat. No. 5,366,504).

In use, stent 20 can be used, e.g., delivered and expanded, using a catheter delivery system. Catheter systems are described in, for example, Wang U.S. Pat. No. 5,195,969, Hamlin U.S. Pat. No. 5,270,086, and Raeder-Devens, U.S. Pat. No. 6,726,712. Stents and stent delivery are also exemplified by the Radius® or Symbiot® systems, available from Boston Scientific Scimed, Maple Grove, Minn.

While a number of embodiments have been described above, the invention is not so limited.

In some embodiments, bands 22 and connectors 24 can have different microstructures. For example, bands 22 and connectors 24 can have different grain sizes, with the grains in the bands being larger than the grains in the connectors. As a result, connectors 24 have a higher yield strength than the yield strength of bands 22, since grain size is typically inversely related to yield strength. The high yield strength of connectors 24 allows them to have small cross-sectional sizes, which allows them to easily deform so that stent 20 can conform well to a vessel that is not straight. The yield strength and the section size are balanced to allow connectors 24 to easily deform while remaining resistant to fracture. In comparison, the low yield strength of bands 22 reduces elastic recoil when stent 20 is crimped to a delivery system and during in vivo expansion. The yield strength and the section size of bands 22 are balanced to provide good resistance to radial compression and to control elastic recoil. Stents having different grain sizes and methods of making the stents are described in commonly assigned U.S. patent application Ser. No. 10/961,289 filed on Oct. 8, 2004.

Stent 20 can include more than one layer. For example, a stent can include a first "structural" layer, such as 316L stainless steel or PERSS®, and a second layer of a radiopaque element. The radiopaque layer can be formed after the heat treatment to prevent, e.g., separation due to thermal expansion differences. Either layer can be the inner or the outer layer, and either layer or both layers can include the microstructures as described above. A three-layered stent can include a layer including a radiopaque element formed between two structural layers.

Stent 20 can also be a part of a covered stent or a stent-graft. In other embodiments, stent 20 can include and/or be attached to a biocompatible, non-porous or semi-porous polymer matrix made of polytetrafluoroethylene (PTFE), expanded PTFE, polyethylene, urethane, or polypropylene.

Stent 20 can include a releasable therapeutic agent, drug, or a pharmaceutically active compound, such as described in U.S. Pat. No. 5,674,242, U.S. Ser. No. 09/895,415, filed Jul. 2, 2001, and U.S. Ser. No. 10/232,265, filed Aug. 30, 2002. The therapeutic agents, drugs, or pharmaceutically active compounds can include, for example, anti-thrombogenic agents, antioxidants, anti-inflammatory agents, anesthetic agents, anti-coagulants, and antibiotics.

All publications, references, applications, and patents referred to herein are incorporated by reference in their entirety.

Other embodiments are within the claims.

What is claimed is:

1. An endoprosthesis consisting of a material and comprising:
    a plurality of circumferentially-oriented bands, the bands formed of the material, each band including two curved portions and a straight portion connecting the two curved portions wherein the material of the curved portions and straight portion has a first grain size, the straight portion having a first width and at least one curved portion having a second width; and
    a plurality of connectors formed of the material, the connectors extending between adjacent bands; wherein the material of the connectors has a second grain size that is smaller than the first grain size
    wherein the second width is greater than the first width; and
    the first width extends uniformly along an axial length region of the straight portion;
    wherein the curved portions and straight portion have a first yield strength and the connectors have a second yield strength that is greater than the first yield strength.

2. The endoprosthesis of claim 1 having a second width to first width ratio that is greater than 1 and less than 3.

3. The endoprosthesis of claim 1 having a second width to first width ratio that is greater than 1.05.

4. The endoprosthesis of claim 1 wherein a second width to first width ratio is greater than 1.1.

5. The endoprosthesis of claim 4 wherein the first yield strength is greater than 70 kilopounds per square inch.

6. The endoprosthesis of claim 1 wherein a second width to first width ratio is greater than 1.5.

7. The endoprosthesis of claim 6 wherein the first yield strength is greater than 70 kilopounds per square inch.

8. The endoprosthesis of claim 1 wherein a second width to first width ratio is greater than 1.75.

9. The endoprosthesis of claim 8 wherein the first yield strength is greater than 70 kilopounds per square inch.

10. The endoprosthesis of claim 1 wherein the first yield strength is greater than 55 kilopounds per square inch.

11. The endoprosthesis of claim 10 wherein the first yield strength is greater than 65 kilopounds per square inch.

12. The endoprosthesis of claim 11 wherein the first yield strength is greater than 70 kilopounds per square inch.

13. The endoprosthesis of claim 1 wherein the first yield strength is greater than 50 kilopounds per square inch and less than 150 kilopounds per square inch.

14. The endoprosthesis of claim 1 wherein the curved portions and straight portions comprise a material selected from the group consisting of stainless steel, stainless steel alloyed with a radiopaque element, nickel alloy, niobium alloy, and titanium alloy.

15. The endoprosthesis of claim 1, wherein each circumferentially-oriented band includes a plurality of curved portions and a plurality of straight portions connecting adjacent curved portions to form a generally sinusoidal pattern.

16. The endoprosthesis of claim 15 having a second width to first width ratio that is greater than 1.1.

17. The endoprosthesis of claim 15 wherein the first yield strength greater than 65 kilopounds per square inch.

18. The endoprosthesis of claim 14 wherein the first yield strength of greater than 70 kilopounds per square inch.

19. The endoprosthesis of claim 1, wherein the circumferentially-oriented band includes a plurality of curved portions and a plurality of straight portions connecting the curved portions, each straight portion further having a length; and
wherein each band has an aggregate curved portion width to straight portion length ratio, calculated by dividing an average curved portion width by a sum of lengths of the straight portions, that is greater than 0.01.

20. The endoprosthesis of claim 19 wherein the aggregate curved portion width to straight portion length ratio is greater than 0.015.

21. The endoprosthesis of claim 19 wherein the first yield strength is greater than 65 kilopounds per square inch.

22. The endoprosthesis of claim 21 wherein the first yield strength is greater than 70 kilopounds per square inch.

23. An endoprosthesis consisting of a material and comprising:
a plurality of circumferentially-oriented bands, the bands formed of the material, each band including a plurality of curved portions and a plurality of straight portions connecting adjacent curved portions to form a generally sinusoidal pattern, the straight portions having a first average width and the curved portions having a second average width, and
a plurality of connectors formed of the material, the connectors extending between adjacent bands;
wherein a width ratio calculated by dividing the second average width by the first average width is greater than 1.05, and the curved portions and straight portion having a first yield strength of greater than 55 kilopounds per square inch; and
wherein the connectors have a second yield strength that is greater than the first yield strength wherein the material of the curved portions and straight portions has a first grain size and wherein the material of the connectors has a second grain size that is smaller than the first grain size.

24. The endoprosthesis of claim 23 wherein the width ratio is greater than 1.1.

25. The endoprosthesis of claim 23 wherein the first yield strength is greater than 70 kilopounds per square inch.

26. A stent, the stent comprising a plurality of bands and a plurality of connectors, the plurality of connectors engaging adjacent bands,
each band comprising a plurality of straight portions, each straight portion engaged to another straight portion by a curved portion, each straight portion having a first width, each curved portion having a second width, the second width being greater than the first width; and
each connector having a third width, the third width being less than the first width;
each of the curved portions and straight portions having a first yield strength wherein a material of the curved portions and straight portions has a first grain size each of the connectors having a second yield strength greater than the first yield strength wherein a material of the connectors has a second grain size that is smaller than the first grain size.

27. The stent of claim 26, wherein a ratio of the second width to the first width is greater than about 1.

28. The stent of claim 26, each band having a band width of at least about 0.03 mm.

* * * * *

UNITED STATES PATENT AND TRADEMARK OFFICE
CERTIFICATE OF CORRECTION

| | |
|---|---|
| PATENT NO. | : 8,435,280 B2 |
| APPLICATION NO. | : 11/095004 |
| DATED | : May 7, 2013 |
| INVENTOR(S) | : Daniel J. Gregorich |

It is certified that error appears in the above-identified patent and that said Letters Patent is hereby corrected as shown below:

In the Claims:

Column 10, Line 34, insert --and-- after the word --size--.

Signed and Sealed this
Sixteenth Day of July, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,435,280 B2 | Page 1 of 1 |
| APPLICATION NO. | : 11/095004 | |
| DATED | : May 7, 2013 | |
| INVENTOR(S) | : Gregorich | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1376 days.

Signed and Sealed this
Second Day of June, 2015

Michelle K. Lee
*Director of the United States Patent and Trademark Office*